(12) United States Patent
Yie et al.

(10) Patent No.: US 8,618,341 B2
(45) Date of Patent: Dec. 31, 2013

(54) PROCESS OF PRODUCING LIQUID FUEL FROM CELLULOSIC BIOMASS

(75) Inventors: Hongping Yie, Huaibei (CN); Meg M. Sun, San Diego, CA (US); Zuolin Zhu, San Diego, CA (US)

(73) Assignee: China Fuel (Huaibei) Bioenergy Technology Development Co. Ltd, Huaibei, Anhui (CN)

( * ) Notice: Subject to any disclaimer, the term of this patent is extended or adjusted under 35 U.S.C. 154(b) by 1122 days.

(21) Appl. No.: 12/534,288

(22) Filed: Aug. 3, 2009

(65) Prior Publication Data
US 2009/0326286 A1  Dec. 31, 2009

Related U.S. Application Data

(63) Continuation of application No. PCT/CN2007/001118, filed on Apr. 6, 2007.

(30) Foreign Application Priority Data

Feb. 1, 2007  (CN) .......................... 2007 1 0006858

(51) Int. Cl.
C10G 1/06  (2006.01)
C07C 1/20  (2006.01)
C08H 7/00  (2011.01)

(52) U.S. Cl.
USPC ............. 585/240; 585/242; 44/605; 502/159; 502/507; 530/503; 127/39

(58) Field of Classification Search
USPC ........... 585/240, 242; 502/159, 507; 530/503, 530/507; 44/605; 127/39, 42, 44, 46.1
See application file for complete search history.

(56) References Cited

U.S. PATENT DOCUMENTS 5,026,927 A * 6/1991 Andrews et al. ............... 568/863
5,536,325 A * 7/1996 Brink ............................. 127/43
(Continued)

FOREIGN PATENT DOCUMENTS

CA  1 175 820 A  9/1984
CN  1629300 A  6/2005
(Continued)

OTHER PUBLICATIONS

Ryoo R., Joo S.H., Jun S., Synthesis of Highly Ordered Carbon Molecular Sieves via Template-Mediated Structural Transformation, Sep. 1999, The Journal of Physical Chemistry B, vol. 103, Num 37, pp. 7743-7746.*
A. Fukuoka, P.L. Dhepe, Catalytic Conversion of Cellulose into Sugar Alcohols, 2006, Angew. Chem. Int. Ed., vol. 45, pp. 5161-5163.*

(Continued)

Primary Examiner — Nina Bhat
Assistant Examiner — Jonathan Miller
(74) Attorney, Agent, or Firm — Hamre, Schumann, Mueller & Larson, P.C.

(57) ABSTRACT

A liquid fuel production process from cellulosic biomass comprises the following steps: (1) providing a mixture of cellulose and water; (2) subjecting the obtained mixture to hydrolysis and catalytic hydrogenation under the presence of acid to obtain mono-sugar alcohol and optional solid material lignin, or subjecting the obtained mixture to hydrolysis to obtain monosaccharide; (3) esterifying the obtained mono-sugar with $C_2$-$C_5$ organic acid to obtain a liquid fuel II, or subjecting the obtained mono-sugar alcohol or monosaccharide to dehydration/hydrogenation to obtain an organic liquid fuel I consisting of alkanes. This process avoids the loss of organic carbon atoms during fermentation, and the sugar derived from cellulosic biomass can be converted to organic carbon in the liquid fuel. The lignin produced by the process can be used for preparing aromatics.

29 Claims, 1 Drawing Sheet

(56) References Cited

U.S. PATENT DOCUMENTS

| | | | |
|---|---|---|---|
| RE37,329 E * | 8/2001 | Gubitosa et al. | 502/185 |
| 7,678,950 B2 * | 3/2010 | Yao et al. | 585/240 |
| 7,998,339 B2 * | 8/2011 | Myllyoja et al. | 585/240 |
| 8,053,615 B2 * | 11/2011 | Cortright et al. | 585/240 |
| 2005/0065337 A1 * | 3/2005 | Werpy et al. | 536/128 |

FOREIGN PATENT DOCUMENTS

| | | |
|---|---|---|
| CN | 1633334 A | 6/2005 |
| CN | 1807554 A | 7/2006 |
| CN | 101012387 A | 8/2007 |
| WO | WO 2005/021475 A1 | 3/2005 |
| WO | WO 2007/095787 A1 | 8/2007 |

OTHER PUBLICATIONS

M. B. Valenzuela, C. W. Jones, P. K. Agrawal, Batch Aqueous-Phase Reforming of Woody Biomass, 2006, Energy & Fuels, vol. 20, pp. 1744-1752.*

International Search Report of PCT/CN2007/001118, dated Nov. 15, 2007.

Written Opinion of the International Searching Authority of PCT/CN2007/001118, dated Nov. 15, 2007.

Huber et al. "An overview of aqueous-phase catalytic processes for production of hydrogen and alkanes in a biorefinery." Catalysis Today, vol. 111, 2006, pp. 119-132.

Fukuoka et al. "Catalytic Conversion of Cellulose into Sugar Alcohols." Angew. Chem. Int. Ed. vol. 45, 2006, pp. 5161-5163.

* cited by examiner

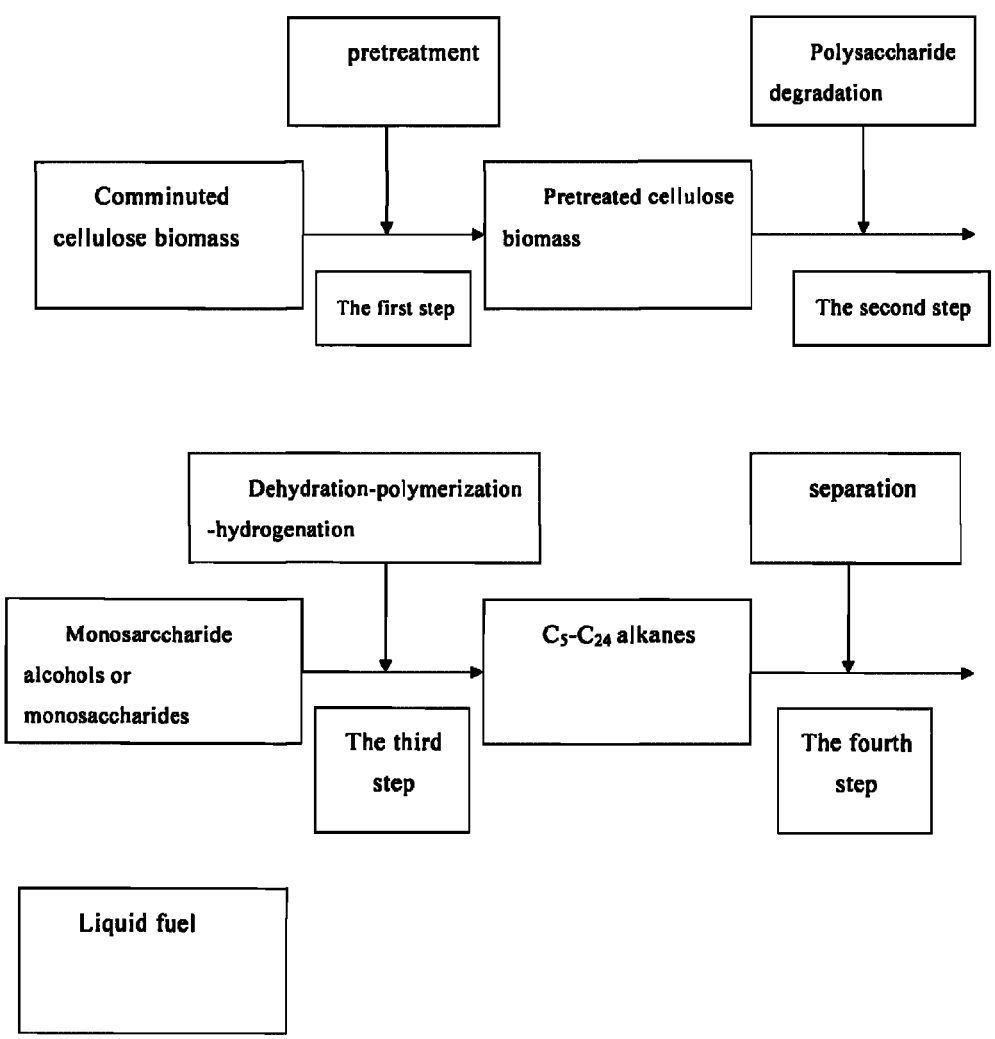

PROCESS OF PRODUCING LIQUID FUEL FROM CELLULOSIC BIOMASS

TECHNICAL FIELD

The present invention relates to a novel process of producing liquid fuel by refining biomass, more particularly to a process which is capable of converting all organic carbons of all the sugar components in cellulosic biomass into liquid fuel, and further relates to a low-cost process of producing highly pure lignin which can be further used for producing a variety of aromatic compounds or be converted into liquid fuel.

BACKGROUND ART

Since the beginning of this century, the global consumption of unrenewable energy sources such as fossil energy sources, for example, coal and oil, and nuclear energy is growing rapidly. As fossil energy sources have arrived at or are approaching to their peaks of supply, mankind has to face the most vital turning point in history, due to both the incoming energy crisis and the global warming which is regarded as the prime cause of various synoptic disasters around the world in recent years and may be attributed largely to the warming gas, i.e. carbon dioxide, most of which originates from fossil energy sources. Therefore, new renewable energy sources must be developed and utilized so as to ensure the continuing existence and sustainable development of human beings.

Great importance has been attached to renewable energy resources all over the world. Biomass derived ethanol fuel is becoming a member of the technical field of liquid fuel, and the processes of producing ethanol fuel from starch and cellulose are under modification and improvement. Particularly, after we developed a technology for rapid pretreatment of cellulosic biomass and a corresponding novel production process (Patent Application No. 200610008062.2, PCT/CN2006/001129), the cost of producing ethanol fuel from cellulosic biomass in industrial scale is expected to be comparable to that of starch derived ethanol fuel, and a booming development of the production of ethanol fuel from cellulosic biomass is promising.

The current process of producing ethanol liquid fuel by fermentation of the starting material cellulosic biomass or starch comprises four major steps as follows: the first step involves pretreatment, the second step is the hydrolysis of the high molecular polymer of saccharide into monosaccharide, the third step is the fermentation of monosaccharide into ethanol, and the fourth step is the separation and dehydration of ethanol to give ethanol fuel. The production of biomass derived butanol fuel shares the same procedure.

The loss of organic carbons in the production process via fermentation is tremendous for both ethanol and butanol. When hexose is used as the monosaccharide, one third of the organic carbons are converted into inorganic carbons of carbon dioxide during fermentation. When pentose is used as the monosaccharide (xylose), sixty percent of the organic carbons are converted into inorganic carbons of carbon dioxide during fermentation. As to another pentose, namely arabinose in cellulosic biomass, it is totally lost due to the lack of good zymogens that can be used for its conversion. In addition, ethanol fuel is produced at high cost owing to the difficulty in dehydration of ethanol. In order to make better use of biomass energy sources, it is necessary to develop a new production process which can avoid the loss of organic carbons.

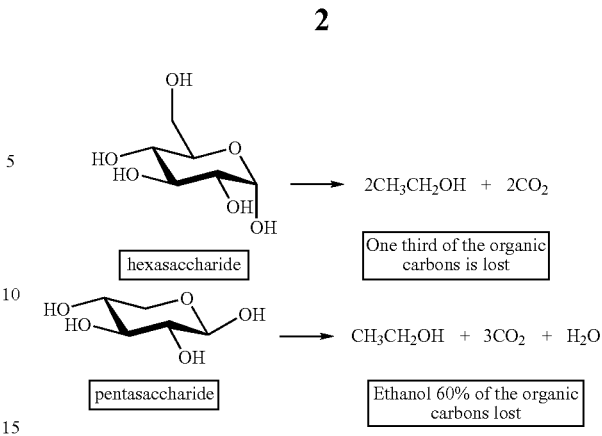

With coal being far more than oil in terms of storage on the earth, it may be predicted that a wide range of coal chemical engineering projects and production bases will rise in full scale, and a lot of hydrogen will be produced as the byproduct. Meanwhile, as the technology of producing hydrogen from coal will be further developed, lower cost will be achieved. Moreover, along with the development of other scientific technologies, the technology of directly producing hydrogen using solar energy will be gradually improved, and the cost will be lowered steadily. New economical and reliable technologies of power production will emerge one after another, resulting in the rapid reduction of the cost for the production of hydrogen by electrolysis. However, it is rather difficult to transport and utilize pure hydrogen. Storing hydrogen in hydrocarbon compounds is one of the best choices to store hydrogen. Thus, one of the most important applications of hydrogen will possibly be the production of biomass liquid fuel and other applications in the field of biomass.

Another consideration is the final cost effectiveness of cellulose hydrolases. Although cellulose hydrolases have already been much more cost effective than previous years thanks to the rapid development of biological technologies and the hard work done by scientific and technical workers in recent years, their cost effectiveness is still rather poor as compared with that of starch hydrolases. It needs further consideration as to whether it is possible or necessary to develop a cellulose hydrolase with high effectiveness. The fact is that cellulosic biomass is a basic energy source upon which the living of animal on the earth relies, and it evolves gradually to a life which is resistant to all cellulose hydrolases. If a super microorganism capable of breaking up cellulosic biomass readily were made successfully, the doomsday of higher animals and plants would come once this super microorganism happened to break into nature out of man's carelessness. Therefore, it is not possible that a cellulose hydrolase with perfect effect will be developed in near future, and the cost of cellulose hydrolases will not be decreased to the level of starch hydrolases. Thus, it is necessary to develop alternative processes of degrading cellulose.

Dehydration and polymerization of monosaccharides and polyols in the presence of acid catalysts are among the most common organic reactions in organic chemistry. The novel process of producing liquid fuel as disclosed in the present invention takes advantage of the undesirable side reactions of saccharides and polyols under acidic conditions, which reactions the scientific and technical workers previously made every effort to avoid. For example, hexose is converted into methylolfurfural under acidic conditions, and pentose is converted into furfural under acidic conditions, etc. These carbonyl compounds will further polymerize to produce organic compounds containing more carbons.

SUMMARY OF THE INVENTION

One object of the present invention is to provide a highly effective process of producing liquid fuel from cellulosic biomass, wherein the process can convert all organic carbons of all sugar components in cellulosic biomass, avoiding the conversion of organic carbons in monosaccharide into inorganic carbons, i.e. carbon dioxide as in the fermentation process which leads to serious loss of organic carbons.

Another object of the present invention is to provide a process of producing highly pure lignin with low cost.

In one aspect of the invention, a highly effective process is provided for producing liquid fuel from cellulosic biomass, comprising:

the first step: a mixture of cellulosic biomass and water is provided, wherein the amount of cellulosic biomass in water is 1-60 w.t. %;

the second step: step (a) or (b) as follows is carried out:

(a) the mixture obtained in the first step is catalytically hydrogenated and hydrolyzed under acidic conditions to produce a liquid product, namely a monosaccharide alcohol solution, and an optional solid product, namely lignin; or (b) the mixture obtained in the first step is hydrolyzed to produce monosaccharides;

the third step: the monosaccharide alcohols or monosaccharides obtained in the second step undergo the following reactions:

(i) the monosaccharide alcohols obtained in (a) of the second step are esterified with a C2-C5 organic acid to produce liquid fuel II which is the esterification product of monosaccharide alcohols; or (ii) the monosaccharide alcohols obtained in (a) or the monosaccharides obtained in (b) of the second step undergo the dehydroxylation-polymerization-hydrogenation to produce liquid fuel I which is an organic product of alkanes.

In one embodiment of the invention, the process further comprises pretreatment of the cellulosic biomass starting material to give the mixture of cellulosic biomass and water as described in the first step, wherein the process for pretreatment is preferably selected from physical chemical processes such as high temperature acid/base process, high temperature acid/base vapor explosion with high temperature ammonia vapor explosion preferred, ambient acid/base ultrasonic wave with ambient ammonia ultrasonic wave preferred, ambient acid/base microwave with ambient ammonia microwave preferred, ammonia recycling flow and combinations thereof; or physical processes alone, with ambient ultrasonic wave, ambient microwave, high temperature vapor explosion and combinations thereof preferred.

In one embodiment of the invention, the catalytic hydrogenation in (a) of the second step is carried out in the presence of 0.1 w.t. %-2.0 w.t. % of acid as calculated based on the weight of the cellulosic biomass; and/or The hydrogenation catalyst of the catalytic hydrogenation in (a) of the second step amounts to 0.1 w.t. %-20 w.t. % of the cellulosic biomass; and/or The hydrogen pressure in (a) of the second step ranges from 1 to 200 atm.; and/or The reaction temperature in (a) of the second step ranges from 0 to 200° C.; and/or The reaction time in (a) of the second step ranges from 1 to 100 hours; and/or The hydrolyzation in (b) of the second step is catalyzed by an acid or an enzyme.

In one embodiment of the invention, the hydrogenation catalyst in (a) of the second step includes:

A heterogeneous catalyst comprising a transition metal dispersed on its support wherein the transition metal is selected from ruthenium, nickel, platinum, palladium and combinations thereof; or A homogeneous catalyst comprising a complex of ruthenium with triphenyl phosphine, a complex of ruthenium with sulfonated phenyl phosphine and combinations thereof.

In one embodiment of the invention, the support of the heterogeneous catalyst is actived carbon prepared by using saccharide as starting material; and/or The amount of the transition metal in the heterogeneous catalyst is 0.1-5.5 w.t. % of the support.

In one embodiment of the invention, the actived carbon is prepared as follows:

(A) The saccharide is dehydrated for 16-20 hours at 350-500° C. in an inert atmosphere to give crude actived carbon;

(B) The crude actived carbon obtained from step (A) is crushed and put into concentrated sulfuric acid at a concentration of >96% up to that of oleum in inert atmosphere to remove residual acid soluble species, giving acid treated actived carbon;

(C) The acid treated actived carbon from step (B) is washed until no sulfate ion is detected, and then dried to give actived carbon;

wherein the inert atmosphere is preferably nitrogen;

wherein the washing in step (C) is carried out using heat distilled water.

In one embodiment of the invention, the molar ratio between the monosaccharide alcohols and the C2-C5 organic acid ranges from 1:1 to 1:10 in (i) of the third step; and/or The reaction in (i) of the third step is carried out in the presence of a non-nucleophilic inorganic strong acid catalyst or an acidic ion exchange resin catalyst; and/or The reaction in (i) of the third step is carried out at 15° C. to 200° C.; and/or The dehydroxylation-polymerization-hydrogenation in (ii) of the third step are carried out in the presence of an acid of which the molar ratio to the monosaccharide alcohols or monosaccharides is 1:1-1:20; and/or The dehydroxylation-polymerization-hydrogenation in (ii) of the third step are carried out at 100° C.-300° C.; and/or The dehydroxylation-polymerization-hydrogenation in (ii) of the third step are carried out in the presence of a catalyst amounting to 0.1-20 w.t. % of the monosaccharide alcohols or monosaccharides; and/or The dehydroxylation-polymerization-hydrogenation in (ii) of the third step are carried out for 10-100 hours; and/or The organic product of alkanes are further separated from water phase to give separated liquid fuel I in (ii) of the third step.

In another aspect of the invention, a process of producing lignin is provided, comprising:

(1) A mixture of cellulosic biomass and water is provided, wherein the amount of cellulosic biomass in water is 1-60 w.t. %;

(2) The mixture obtained in step (1) is catalytically hydrogenated and hydrolyzed under acidic conditions to produce a solid product, namely lignin, and liquid product, namely monosaccharide alcohols.

In one embodiment of the invention, the mixture in step (1) is obtained as follows:

The cellulosic biomass starting material is pretreated to give the mixture of cellulosic biomass and water as described in step (1), wherein the pretreatment is done by a physical process; and/or The catalytic hydrogenation in step (2) is carried out in the presence of an acid amounting to 0.1 w.t. %-2.0 w.t. % of the cellulosic biomass; and/or The hydrogenation catalyst of the catalytic hydrogenation in step (2) amounts to 0.1 w.t. %-20 w.t. % of the cellulosic biomass; and/or The hydrogen pressure in step (2) ranges from 1 to 200 atm.; and/or The reaction temperature in step (2) ranges from 0 to 200° C.; and/or The reaction time in step (2) ranges from 1 to 100 hours; wherein the physical pretreatment process is preferably selected from ambient ultrasonic wave process, ambient microwave process, high temperature vapor explosion process and combinations thereof.

In one embodiment of the invention, the hydrogenation catalyst in step (2) includes:

A heterogeneous catalyst comprising a transition metal dispersed on its support wherein the transition metal is selected from ruthenium, nickel, platinum, palladium and combinations thereof; or A homogeneous catalyst which includes a complex of ruthenium with triphenyl phosphine, a complex of ruthenium with sulfonated phenyl phosphine and combinations thereof;

wherein the support of the heterogeneous catalyst is preferably actived carbon prepared using saccharide as starting material.

For example, the highly effective process of producing liquid fuel from cellulosic biomass according to the invention includes the following steps:

the first step: Cellulosic biomass is pretreated before a mixture of cellulosic biomass and water is provided, wherein the amount of cellulosic biomass in water is 1-60 w.t. %;

the second step: Step (a) or (b) as follows is carried out:

(a) The mixture obtained in the first step is catalytically hydrogenated and hydrolyzed under acidic conditions to produce a liquid product, namely a solution of monosaccharide alcohol, and an optional solid product, namely lignin, wherein the existence of lignin depends on the pretreatment of the cellulosic biomass, and the monosaccharide alcohols involves all pentoses and hexoses, such as glucitol, xylitol, mannitol, galactitol and arabitol, etc.; or (b) The mixture obtained in the first step is hydrolyzed to produce monosaccharides which include glucose, xylose, mannitose, galactose and arabinose, etc.;

the third step: The monosaccharide alcohols or monosaccharides obtained in the second step undergo the following reactions:

(i) The monosaccharide alcohols obtained in (a) of the second step are esterified with a C2-C5 organic acid to produce liquid fuel II which is the esterification product of monosaccharide alcohols; or (ii) The monosaccharide alcohols obtained in (a) or the monosaccharides obtained in (b) of the second step are dehydroxylated, polymerized and hydrogenated to produce liquid fuel I, wherein the liquid fuel I is an organic product of alkanes which has a boiling point range covering those of gasoline and diesel oil, and contains C5-C24 alkanes as its main components, which is substantially identical to those of commercial gasoline and diesel oil currently available; and the reaction involving dehydroxylation-polymerization-hydrogenation is a very complex process in which, for monosaccharide alcohols, dehydroxylation is the starting step, and the intermediates thus produced undergo relevant polymerization to give products with a multiple of unsaturated bonds that are reduced to saturated alkanes via hydrogenation, while for monosaccharides, hydrogenation and dehydroxylation occur simultaneously, and the intermediates thus produced undergo relevant polymerization to give products with a multiple of unsaturated bonds that are reduced to saturated alkanes via hydrogenation.

Meanwhile, the first step and (a) of the second step of the process constitute a process of producing highly pure lignin as a byproduct.

BRIEF DESCRIPTION OF THE DRAWING

The appended FIG. 1 shows a process flow chart for producing liquid fuel from cellulosic biomass.

BEST MODES FOR CARRYING OUT THE INVENTION

Cellulosic biomass which is used as the starting material according to the invention is defined as biomass containing cellulose. Here, biomass refers to substances having their edible parts removed but still rich in biomass energy, such as crop straw, bamboo, reed, trees, leaves, weeds and hydrophytes, etc. The main constituents of such cellulosic biomass are polysaccharide celluloses, hemicelluloses and lignin of polyaromatic compounds.

In the production process disclosed in the invention, any process can be used to pretreat cellulosic biomass, as long as the object of the invention will not be obstructed thereby. Specific pretreatment methods include but not limited to acid/base process, high temperature vapor explosion under acidic condition, high temperature vapor explosion, high temperature ammonia vapor explosion, ambient acid/base ultrasonic wave, ambient ultrasonic wave, ambient acid/base microwave, ambient microwave, ozone process, etc. The object of pretreatment according to the invention varies. If monosaccharides are to be prepared in the next step of hydrolyzation of cellulose and hemicellulose, the object is to remove lignin that impacts hydrolyzation, dissociate hemicellulose and destroy the crystalline structure of cellulose, so as to enlarge the accessible surface of saccharide polymers in biomass and promote the rate of hydrolyzation, wherein the procedure is carried out in basic condition which means pH is not less than 7. If monosaccharide alcohols are to be prepared in the next step of hydrogenation and hydrolyzation, the object is to destroy the structure of cellulosic biomass, particularly the crystalline structure of cellulose, so as to enlarge the accessible surface of saccharide polymers in biomass and promote the rate of hydrolyzation.

The pretreatment processes described above are intended only to exemplify in part the pretreatment methods of the invention. Based on the foregoing examples, those skilled in the art may obtain the pretreated cellulosic biomass via modified methods or common technologies. For example, a combination of the foregoing pretreatment processes may be used. As another example, the resulting pretreated cellulosic biomass may be purified by further filtration, washing, etc.

According to the production process disclosed in the invention, the reaction for preparing monosaccharide alcohols is generally carried out in water, wherein: the solid content in the liquid may be 1-60%; the acid used to catalyze the hydrogenation and hydrolyzation of polysaccharide cellulose and hemicellulose into monosaccharide alcohols may be an inorganic or organic acid which generally amounts to 0.1%-2.0% by dry weight of cellulosic biomass and includes but not limited to sulfuric acid, phosphoric acid, phosphorous acid, hypophosphorous acid, acetic acid, etc., or their combinations; the pressure of hydrogen used is 1-200 atm; and the catalyst for hydrogenation may be a homogeneous or heterogeneous catalyst, including but not limited to homogeneous catalysts such as various complexes of ruthenium with triphenyl phosphine, sulfonated phenyl phosphine, etc., and heterogeneous catalysts formed by dispersing transition metals such as ruthenium (Ru), nickel (Ni), platinum (Pt) and palladium (Pd), at a typical loading of 0.1%-5.5% by weight, on various supports which may be actived carbon, silicon dioxide (silica gel), industrial acidic zeolite, alumina, high molecular polymers containing triphenyl phosphine, etc.

In the present invention, the inventors have found for the first time that such new transition-metal catalysts as ruthenium (Ru), nickel (Ni), platinum (Pt), palladium (Pd) and the like supported on actived carbon which is prepared using saccharide as starting material exhibits the best effect.

According to the production process disclosed in the invention, the saccharide used for preparing actived carbon may be various monosaccharides, such as trioses, tetroses, pentoses and hexoses, for example, glucose; and various disaccharides, such as disaccharides comprised of the same type of saccharides and disaccharides comprised of different types of saccharides, for example, sucrose. The process of preparing actived carbon is not specifically limited, as long as the object of the invention is not obstructed. Nevertheless, it is preferred that the saccharide is generally dehydrated under the protection of nitrogen stream at high temperature in the range of 350-500° C.; the crude actived carbon resulting from dehydration is generally washed with concentrated sulfuric acid at a concentration of >96% up to that of oleum under the protection of nitrogen stream to remove acid soluble species; and after acid washing, the actived carbon is rinsed with heat distilled water until no acid radical can be detected.

Heterogeneous catalysts are generally prepared using water soluble salts of transition metals, including but not limited to ruthenium chloride, hexammine ruthenium chloride, tetrammine platinum nitrate, tetrammine palladium nitrate, nickel chloride, etc. During the preparation, the support and the water soluble salt of the transition metal is generally mixed evenly in deionized water before halogen ions are removed completely by washing with warm deionized water. Activation of the catalyst is generally carried out in hydrogen stream at 200-480° C. for 2-16 hours.

According to the production process disclosed in the invention, although cellulose hydrolase is generally used as the catalyst for hydrolyzing polysaccharide cellulose and hemicellulose into monosaccharides, other enzymes such as glucosidase may also be added, and acid such as sulfuric acid, phosphoric acid and hydrochloric acid may also be used. The conditions for the hydrolyzation reaction in the invention are not specifically limited, so long as the object of the invention is not obstructed. In particular, for example, the process includes the following steps: first, solid cellulose and hemicellulose from which lignin is removed by pretreatment are formed into an aqueous suspension or mixture; secondly, if a hydrolase is used, an appropriate amount of hydrolase is added into the above suspension or mixture (neither the type nor the amount of the hydrolase is specifically limited, as long as the object of the invention is not obstructed), after which the hydrolyzation is generally carried out at 25-50° C. and pH 4.5-7.5, and the reaction time is not specifically limited, as long as the object of the invention is not obstructed, e.g. 72±10 hours; thirdly, after the hydrolyzation is completed, the hydrolase is generally precipitated by increasing the temperature, and a solution of monosaccharides is obtained after all solid is filtered out; and in the fourth step, the solution may be concentrated to produce concentrated saccharide solution, or it may be spray dried to give solid monosaccharides. If the hydrolyzation is catalyzed by acid, an appropriate amount of acid is added into the suspension or mixture in the second step wherein the concentration of acid is generally not more than 3% w/w (the lower limit of the acid concentration is not specifically limited, as long as the object of the invention is not obstructed), and the reaction is generally carried out at 150-250° C. with the temperature being not specifically limited, as long as the object of the invention is not obstructed. And in the third step, a base is added to neutralize the acid, and then an aqueous monosaccharide solution is obtained after all solid is filtered out.

According to the production process disclosed in the invention, by way of esterification, monosaccharide alcohols may be converted into novel biodisel oil, i.e. liquid fuel II, as the esterification product of monosaccharide alcohols. The resulting monosaccharide alcohols are generally spray dried to give dry product. C2-C5 organic acids are generally used as the acyl sources for esterification. Nevertheless, anhydrides of these acids are often used as starting material, e.g. acetic anhydride, various propionic anhydrides, various butanoic anhydrides, and various pentanoic anhydrides, etc. In general, these anhydrides may be used as solvent in the esterification wherein the molar ratio between monosaccharide alcohols and the anhydride generally ranges from 1:1 to 1:10. As to the catalyst of the esterification, these acids per se may be generally used, or a non-nucleophilic inorganic strong acid may be used, or even an acidic ion-exchange resin may be used. The catalyst as discussed above is not specifically limited, so long as the esterification reaction can be catalyzed thereby. The reaction temperature generally ranges from room temperature to 200° C., more generally from room temperature to 120° C. The esterification reaction may also take place in non-protonic solvent such as benzene. The reaction in benzene is generally carried out in a dehydration reactor at reflux temperature.

The esterification processes discussed above are intended only to exemplify in part the esterification methods of the invention. Based on the foregoing examples, those skilled in the art may obtain the desired esterification product of monosaccharide alcohols according to the invention via modified methods or common technologies. For example, other acyl sources may be used.

According to the production process disclosed in the present invention, by way of dehydroxylation-polymerization-hydrogenation, monosaccharide alcohols may also be converted into hydrocarbons, i.e. liquid fuel I. The acid catalyst used in the dehydroxylation-polymerization-hydrogenation of monosaccharide alcohols may be an inorganic or organic acid, including but not limited to liquid acids such as sulfuric acid, phosphoric acid, hydroiodic acid, phosphorous acid, hypophosphorous acid, acetic acid, etc., and solid acids such as acidic alumina. The molar ratio between the acid and monosaccharide alcohols is in the range of 1:1-20. The catalyst and the reductant are not specifically limited, as long as the object of the invention is not obstructed. Preferably, the catalyst may be supported ruthenium (Ru), nickel (Ni), platinum (Pt) and palladium (Pd), and the reductant may be hydrogen, phosphorous acid, or hypophosphorous acid, etc. The pressure of hydrogen is 1-200 atm. The amount of phosphorous acid or hypophosphorous acid used is generally 1-20 molar equivalents. The reaction of dehydroxylation-polymerization-hydrogenation is generally carried out under the protection of nitrogen, and the reaction temperature is generally in the range of 100-300° C.

The dehydroxylation-polymerization-hydrogenation processes discussed above are only intended to exemplify in part the dehydroxylation-polymerization-hydrogenation methods of the invention. Based on the foregoing examples, those skilled in the art may obtain the desired hydrocarbons according to the invention via modified methods or common technologies. For example, the resulting product may be further purified.

According to the production process disclosed in the invention, if acid containing halogen is used in the dehydroxylation-polymerization-hydrogenation of monosaccharide alcohols, alkyl halides are often contained in the alkane product, therefore the product can not be used as fuel. These alkyl halides may be removed readily. For example, they can be converted into alkenes by eliminating hydrogen halides with a base, or be converted into ethers by condensation.

According to the production process disclosed in the invention, alkanes in the product may be separated by distillation or by standing still till different layers are formed.

According to the production process disclosed in the invention, if polysaccharide cellulose and hemicellulose are catalytically hydrogenized, hydrolyzed and reduced into monosaccharide alcohols using a catalyst with an acidic support, solid lignin having high purity may be separated from the reaction product. After simple rinsing, the purity may be up to 96%. This lignin may be used to prepare the desired various aromatic compounds, and may also be used as the starting material of hydrocracking and liquification to prepare liquid fuel. According to the production process disclosed in the invention, it is known that all technologies for producing oil by direct liquification of coal may be used herein to convert lignin into liquid fuel, wherein both high temperature/high pressure hydrocracking and molten zinc chloride process may be used.

According to the production process disclosed in the invention, if cellulosic biomass is pretreated under basic conditions, the pretreated biomass comprises a solid part and a liquid part, wherein the solid part comprises mainly cellulose and hemicellulose, as well as very little lignin; while the liquid part comprises mainly lignin and hemicellulose, as well as very little cellulose. The solid part and the liquid part may be separated using any traditional separation method.

The pretreatment reaction, the hydrolyzation reaction, as well as the dehydroxylation-polymerization-hydrogenation reaction may be carried out in a batch reactor system, a continuous flow reactor system or a flow through reactor system.

The following examples are intended to provide better understanding of the invention, by no means limiting the disclosure of the invention to those examples.

Biomass used in the following examples includes but not limited to crushed and naturally dried maize straw, broomcorn straw, reed, bamboo, various hard and soft wood, weeds, or wheat straw, soy straw, and cotton straw. The biomass particles are 1.6-2.4 mm in size. In the embodiments, the particles of maize straw are comprised of 36.4 wt % β-glucan, 18.8 wt % xylan, 2.8 wt arabinan, 1.8 wt % glucomannan, 2.2 wt % galactan, 20.2 wt % Klason lignin, 7.0 wt % ash, 3.2 wt % acetyl group, 4.0 wt % protein, and 3.8 wt % uronic acid. The particles of wheat straw are comprised of 33 wt % β-glucan, 45 wt % xylan, 20 wt % Klason lignin; The particles of soy straw are comprised of 41 wt % β-glucan, 23 wt % xylan, 20.8 wt % Klason lignin; The particles of cotton straw are comprised of 41.4 wt % β-glucan, 23.8 wt % xylan, 20.6 wt % Klason lignin.

The contents of saccharide and lignin in solid samples are measured, after acid treatment, using HPLC method (NREL Chemical Analysis and Testing Standard Procedure, 001-004, 1996).

The reaction products are analyzed using GC-MS.

EXAMPLE 1

Preparation of Actived Carbon

A powder of 100 g glucose was heated to 400° C. in nitrogen stream, wherein the color of glucose changed gradually from white to brown and finally to black. This reaction took about 16-20 hours. After heating was ceased, the resulting black solid was cooled to room temperature under the protection of nitrogen and then crushed. Then, the resultant was transferred into 600 ml 99% concentrated sulfuric acid which had been deoxygenated by flushed with nitrogen. Under the protection of nitrogen and slow stirring, the resulting mixture was heated to 150° C. and kept for 15 hours. Then, the mixture was cooled to room temperature before it was diluted with 5 times by volume of distilled water. The temperature was kept not higher than 50° C. The black solid product was washed with heat distilled water until no sulfate ion was detected, and then it was vacuum dried. No metal commonly found in conventional actived carbon such as iron, lead and copper was detected in the actived carbon of the invention. The actived carbon which would be used as a support as described below had a specific surface area of 900-1400 $m^2/g$ and a pore volume of 1.0-2.5 ml/g as measured by conventional methods.

EXAMPLE 2

Preparation of Ruthenium/Actived Carbon Catalyst

A solution of 0.77 g ruthenium trichloride in 1000 ml deionized water was mixed with 10 g actived carbon in Example 1 under the protection of nitrogen. After 2 hours of stirring, the water was evaporated completely, and the resulting solid was washed with deionized water to remove all chlorine ions. The solid catalyst was activated at 400° C. in hydrogen stream to give ruthenium/actived carbon catalyst. The catalyst was sampled and analyzed for three times, which showed that the content of ruthenium was in the range of 3.6-3.9%, of which the average value is 3.8% based on the weight of support.

EXAMPLE 3

Preparation of Platinum/Acidic Alumina Catalyst

A solution of 1.0 g tetrammine platinum nitrate in 100 ml deionized water was mixed with 10 g acidic alumina under the protection of nitrogen. After 2 hours of stirring, the mixture was filtered, and the resulting solid was dried in vacuum at 60° C. for 12 hours. The solid obtained after drying was calcined in helium stream containing 20% oxygen, wherein the temperature was raised under a rate of 1° C./min. to 150° C. and then kept at this temperature for 2 hours. Then, the solid catalyst was activated at 300° C. in hydrogen stream to give platinum/acidic aluminum catalyst. The catalyst was sampled and analyzed for three times, which showed that the content of platinum was in the range of 4.9-5.2%, of which average value is 5.0% based on the weight of support. The analyzing method was a conventional one in which an amount of catalyst was dissolved in aqua regia and diluted to certain concentration before the content of platinum in the catalyst was measured by atomic absorption spectrometry and a working graph was plotted using a control.

EXAMPLE 4

Preparation of Fuel I and Fuel II from Monosaccharide Alcohols

EXAMPLE 4A

Microwave Pretreatment

To a suitable vessel (e.g. PFA (perfluoralkoxy teflon) or PTFE (polytetrafluoroethylene) reaction vessel) was added 20.0 g crushed and naturally dried maize straw and 50 ml deionized water. After sealed, the mixture was treated in a microwave reactor at 1000 W/2.45 GHz for 20 minutes during which the vessel containing the maize straw was shaken continuously. After treatment, the resultant was cooled to room temperature and filtered for later use.

EXAMPLE 4B

Preparation of Monosaccharide Alcohols and Lignin

The maize straw treated in Example 4A was formulated directly with pure water into a 25% suspension based on solid/liquid ratio. Then, to the suspension was added a small quantity of phosphoric acid, amounting to about 0.7% by weight of the maize straw. In the presence of ruthenium/actived carbon catalyst (as prepared in Example 2) which was about 0.6% by weight of maize straw and contained 3.8% ruthenium, the treated maize straw was subjected to catalytically acid-assisted hydrogenation-hydrolyzation, wherein the temperature was 160° C., the hydrogen pressure was 4.5 MPa, and the reaction time was about 2-3 hours. Then, the resultant was cooled to below 10° C., and hydrogen was discharged. After standing still for about 20 minutes, the catalyst totally settled at the bottom of the stainless steel autoclave. Upper part of the solid and liquid were removed and filtered to give a homogeneous aqueous solution. As analyzed by electrically ionized gas chromatography-mass spectrometry (GC-MS) using a derivative of butyl boron ester, most products in the liquid phase were monosaccharide alcohols of which the yield was >95% based on the amount of saccharide that can be converted from cellulose and hemicellulose in the maize straw. Lignin as the solid product resulting from filtration was washed with pure water and vacuum dried to give 3.62 g solid which contained 96.8% lignin as measured by conventional dioxane extraction analysis.

EXAMPLE 4C

Conversion of Monosaccharide Alcohols to Liquid Fuel I

To the liquid product obtained in Example 4B was added about 7 equiv. hydrogen iodide and 5 equiv. phosphorous acid. The mixture reacted at 120° C. and at a hydrogen pressure of 1.6 MPa for about 16 hours. After cooled to room temperature, the hydrogen was discharged, and the reaction product was extracted with methylene chloride. As analyzed by GC-MS, about 20% components of the product contained iodine. The product is divided into two groups by distillation, wherein one group contains iodine while the other doesn't. The iodine-containing group was further analyzed only to find that about 90 mol. % components were compounds having a molecular weight of 212 or 198 ($C_5H_{11}I$: m/e=198, $C_6H_{13}I$: m/e=212) and thus originating from hexose and pentose. The other group containing no iodine was comprised of alkanes containing 5-24 carbon atoms ($C_{11}H_{20}$ m/e=152, $C_{12}H_{22}$ m/e=166, $C_{18}H_{32}$ m/e=248, $C_{24}H_{44}$ m/e=332).

When 2 g alkanes containing iodine was mixed with 0.6 g potassium hydroxide at 140° C. in a sealed reactor for some dozen minutes, and then cooled to below 10° C., no alkane containing iodine was detected in the liquid product and the main resultants were alkenes ($C_5H_{10}$: m/e=70, $C_6H_{12}$: m/e=84) at a yield >96%. The total yield of $C_5$-$C_{24}$ alkanes and alkenes as the product of deiodization was measured to be over 96%. It was likely that part of lignin was dissolved in the aqueous solution and then reduced to saturated alkanes. Or else, the yield should be lower because of loss in the operation.

EXAMPLE 4D

Conversion of Monosaccharide Alcohols to Fuel II

The monosaccharide alcohols obtained in Example 4B were spray dried to remove water. After further vacuum dried at 60° C. for 24 hours, a mixture of monosaccharide alcohols was obtained as a pale grayish yellow solid which was crushed under the protection of nitrogen and then added to a dehydration reactor together with 5 times of toluene (weight/volume ratio) under the protection of nitrogen. 2% concentrated sulfuric acid and about 7 equiv. acetic anhydride were sequentially added therein under stirring. Then dehydration was carried out under reflux. The reflux was continued for about 3 hours after no water was formed. After cooled to 10° C., the reaction product was washed three times with about 1/3 by volume of distilled water. The solution of the reaction product was analyzed by GC-MS, which revealed that the main components of the product were compounds having molecular weights of 434 ($C_{18}H_{26}O_{12}$), 362 ($C_{15}H_{22}O_{10}$), 332 ($C_{14}H_{20}O_9$) and 260 ($C_{11}H_{16}O_7$), etc.

EXAMPLE 5

Preparation of Fuel I from Monosaccharides

EXAMPLE 5A

Ultrasonic Pretreatment

To a suitable vessel was added 20 g powdered and naturally dried maize straw, and then was added 300 ml 15 wt % ammonia as solvent. After sealed, the mixture was treated in a 2 kW/20 kHz ultrasonic reactor. The vessel containing the maize straw was continuously shaken during the treatment. After a 60 minutes treatment, the resulting solid sample was washed with deionized purified water to remove ammonia so that it could be converted to monosaccharides or monosaccharide alcohols as described below.

EXAMPLE 5B

Preparation of Monosaccharide Solution

The solid product obtained in Example 5A was formulated into a suspension having a solid/liquid ratio of 10% using a buffer solution of citrate having pH of 4.8. Then, about 10 wt % Spezyme CP cellulose hydrolase (Genencor Inc., average activity: 30.6 FPU/ml and 20 CBU/ml, 106 mg protein/ ml) and 5% β-glucosidase (Novozyme, activity: 401 U/g). The reaction was carried out at 48-50° C. under slow stirring for 72 hours. After cooled and filtered, the product was analyzed to have 98% monosaccharides and protected by nitrogen for later use.

EXAMPLE 5C

Conversion of Monosaccharides to Fuel I

To the monosaccharide liquid product obtained in Example 5B was directly added about 5 wt. % platinum/acidic alumina catalyst obtained in Example 3. Then, about 1 equiv. hydrogen iodide and 5 equiv. phosphorous acid were added. About 10% v/v acetone was used to aid in dispersing the feed. Stirring (at a rate of 600 rpm) was continued for about 16 hours at 160° C. and at a hydrogen pressure of 6.0 MPa. After cooled to room temperature, the hydrogen was discharged. The reaction product was extracted with methylene chloride and found that the product contained only a small amount of iodine-containing alkanes (m/e=198, m/e=212, m/e=324, m/e=338). After analyzed by GC-MS, it was found by way of comparing the MS data of the product with those in MS data base that m/e=128, m/e=166, m/e=170, m/e=226, m/e=248, m/e=254, m/e=332, m/e=338 and the like were the broad peak area of the main peaks. Small molecular products corresponding to m/e=72, m/e=86 were also detected. They were all $C_5$-$C_{24}$ alkanes.

Industrial Applicability

As compared with conventional processes of producing ethanol fuel by fermentation, the process of producing liquid fuel as disclosed in the invention has the following conspicuous advantages:

1. All of the organic carbons in the monosaccharides or monosaccharide alcohols converted from cellulosic biomass are transformed to the organic carbons in the final liquid fuel according to the invention, while one third of the organic carbons in hexoses and 60% of those in pentoses are lost according to conventional processes of producing ethanol fuel by fermentation;

2. The final product afforded in the third step according to the invention can be easily separated from water as hydrocarbons by standing still and layering after the reaction due to its water insolubility, while in conventional processes of producing ethanol fuel by fermentation, it is difficult for the product ethanol to be separated from water, rendering distillation and dehydration for refining the most-energy-consuming step which is estimated to consume over 50% of the whole energy necessary in the process of producing ethanol fuel (Katzen, R.; Fuels From Biomass and Wastes, 1981, 393-402);

3. The final product obtained in the invention is composed of alkanes which exhibit little erodibility to the engine in contrast to ethanol;

4. Having a wide range of boiling points, the product obtained in the invention includes fractions of both below 200° C. (gasoline section) and above 200° C. (diesel oil section), so that we can prepare the desired liquid fuel of gasoline and diesel oil directly from cellulosic biomass, while only ethanol fuel can be obtained according to the conventional fermentation process;

5. Highly concentrated reactants and a reaction kettle much smaller than a fermentation tank can be used in the invention, and the invention witnesses a faster reaction rate and a much higher production efficiency in contrast to the fermentation process for monosaccharides;

6. The substep (a) of the second step according to the invention exempts the removal of lignin in cellulosic biomass. Although lignin is a strong inhibitor against the cellulose hydrolase, it nearly inflicts no impact on acid-assisted hydrolyzation and hydrogenation reaction under hydrogenation conditions which can not reduce the lignin. Since lignin is insoluble in acid, it can be separated by simple filtration after the reaction. For it is unnecessary to remove lignin, what the pretreatment of cellulosic biomass needs to do is just break the dense structure of cellulosic biomass which can be achieved through a physical pretreatment process alone, e.g. ambient ultrasonic wave, ambient microwave, high temperature vapor explosion. Thus, the cost of pretreatment can be further reduced;

At the same time, a process of producing highly pure lignin as a byproduct is provided via the above method.

The invention claimed is:

1. A highly effective process of producing liquid fuel from a cellulosic biomass, comprising:
   the first step: providing a mixture of cellulosic biomass and water, wherein the amount of the cellulosic biomass in water is 1-60 w.t. %, and wherein the cellulosic biomass comprises cellulose, hemicellulose and lignin;
   the second step: carrying out step (a) as follows:
   (a) the mixture obtained in the first step is catalytically hydrogenated and hydrolyzed under acidic conditions to produce monosaccharide alcohols, and lignin;
   the third step: the monosaccharide alcohols obtained in the second step are subjected to one of the following reactions (i) and (ii):
   (i) the monosaccharide alcohols obtained in (a) of the second step are esterified with a C2-C5 organic acid to produce a liquid fuel II which is an esterification product of the monosaccharide alcohols; and
   (ii) the monosaccharide alcohols obtained in (a) of the second step are subjected to dehydroxylation-polymerization-hydrogenation to produce a liquid fuel I which is an organic product of alkanes.

2. A process of claim 1, further comprising:
   pretreating the cellulosic biomass starting material to give the mixture of cellulosic biomass and water as described in the first step.

3. A process of claim 1, wherein:
   the catalytic hydrogenation in (a) of the second step is carried out in the presence of an acid amounting to 0.1 w.t. %-2.0 w.t. % of the cellulosic biomass.

4. A process of claim 3, wherein:
   the hydrogenation catalyst in (a) of the second step includes one of the following (1) and (2):
   (1) a heterogeneous catalyst comprising a transition metal dispersed on a support,
   wherein the transition metal is selected from ruthenium, nickel, platinum, palladium and combinations thereof; and
   (2) a homogeneous catalyst which includes a complex of ruthenium with triphenyl phosphine, a complex of ruthenium with sulfonated phenyl phosphine and combinations thereof.

5. A process of claim 4, wherein:
   the support of the heterogeneous catalyst is an activated carbon prepared using saccharide as starting material.

6. A process of claim 5, wherein the activated carbon is prepared by a method comprising the steps as follows:
   (A) the saccharide is dehydrated for 16-20 hours at 350-500° C. under an inert atmosphere to give crude activated carbon;
   (B) the crude activated carbon from step (A) is crushed and put into concentrated sulfuric acid at a concentration of >96% in an inert atmosphere to remove acid soluble species, giving acid treated activated carbon; and (C) the acid treated activated carbon from step (B) is washed until no sulfate ion is detected, and then dried to give activated carbon.

7. A process of claim 1, wherein:
a molar ratio between the monosaccharide alcohols and the C2-C5 organic acid ranges from 1:1 to 1:10 in (i) of the third step.

8. The process of claim 3, wherein the hydrogenation catalyst of the catalytic hydrogenation in (a) of the second step amounts to 0.1 w.t. %-20 w.t. % of the cellulosic biomass.

9. The process of claim 1, wherein a hydrogen pressure in (a) of the second step ranges from 1 to 200 atm.

10. The process of claim 1, wherein a reaction temperature in (a) of the second step ranges from 0 to 200° C.

11. The process of claim 4, wherein an amount of the transition metal in the heterogeneous catalyst is 0.1-5.5 w.t. % of the support.

12. The process of claim 1, wherein the reaction in (i) of the third step is carried out in the presence of a non-nucleophilic inorganic strong acid catalyst or an acidic ion exchange resin catalyst.

13. The process of claim 1, wherein the reaction in (i) of the third step is carried out at 15° C. to 200° C.

14. The process of claim 1, wherein the dehydroxylation-polymerization-hydrogenation in (ii) of the third step is carried out in the presence of an acid, wherein a molar ratio between the acid and the monosaccharide alcohols is 1:1-1:20.

15. The process of claim 1, wherein the dehydroxylation-polymerization-hydrogenation in (ii) of the third step is carried out at 100° C. -300° C.

16. The process of claim 1, wherein the dehydroxylation-polymerization-hydrogenation in (ii) of the third step is carried out in the presence of a catalyst amounting to 0.1-20 w.t. % of the monosaccharide alcohols.

17. The process of claim 1, wherein the dehydroxylation-polymerization-hydrogenation in (ii) of the third step is carried out for 10-100 hours.

18. The process of claim 1, wherein in (ii) of the third step, the organic products of alkanes are further separated from water phase to give the separated liquid fuel I.

19. The process of claim 6, wherein the sulfuric acid is oleum.

20. The process of claim 1, wherein the lignin produced in step (a) has a purity of greater than 96%.

21. A process of producing lignin, comprising the steps as follows:
(1) providing a mixture of cellulosic biomass and water, wherein the amount of cellulosic biomass in water is 1-60 w.t. %, and wherein the cellulosic biomass comprises cellulose, hemicellulose and lignin; and
(2) the mixture obtained in step (1) is catalytically hydrogenated and hydrolyzed under acidic conditions to produce lignin, and monosaccharide alcohols.

22. A process of claim 21, wherein:
the mixture in step (1) is obtained by a method comprising the steps as follows:
the cellulosic biomass starting material is pretreated to give the mixture of cellulosic biomass and water as described in step (1), wherein the pretreatment is done by a physical process.

23. A process of claim 22, wherein:
the hydrogenation catalyst in step (2) includes one of the following (i) and (ii):
(i) a heterogeneous catalyst comprising a transition metal dispersed on a support, wherein the transition metal is selected from ruthenium, nickel, platinum, palladium and combinations thereof; and
(ii) a homogeneous catalyst which includes a complex of ruthenium with triphenyl phosphine, a complex of ruthenium with sulfonated phenyl phosphine and combinations thereof.

24. The process of claim 21, wherein the catalytic hydrogenation in step (2) is carried out in the presence of an acid amounting to 0.1 w.t. %-2.0 w.t. % of the cellulosic biomass.

25. The process of claim 21, wherein the hydrogenation catalyst of the catalytic hydrogenation in step (2) amounts to 0.1 w.t. %-20 w.t. % of the cellulosic biomass.

26. The process of claim 21, wherein a hydrogen pressure in step (2) ranges from 1 to 200 atm.

27. The process of claim 21, wherein a reaction temperature in step (2) ranges from 0 to 200° C.

28. The process of claim 21, wherein the reaction time in step (2) ranges from 1 to 100 hours.

29. The process of claim 21, wherein the lignin produced in step (1) has a purity of greater than 96%.

* * * * *